Jan. 20, 1970 H. C. BROWNELL Plant Pat. 2,960
ROSE PLANT
Filed March 22, 1968
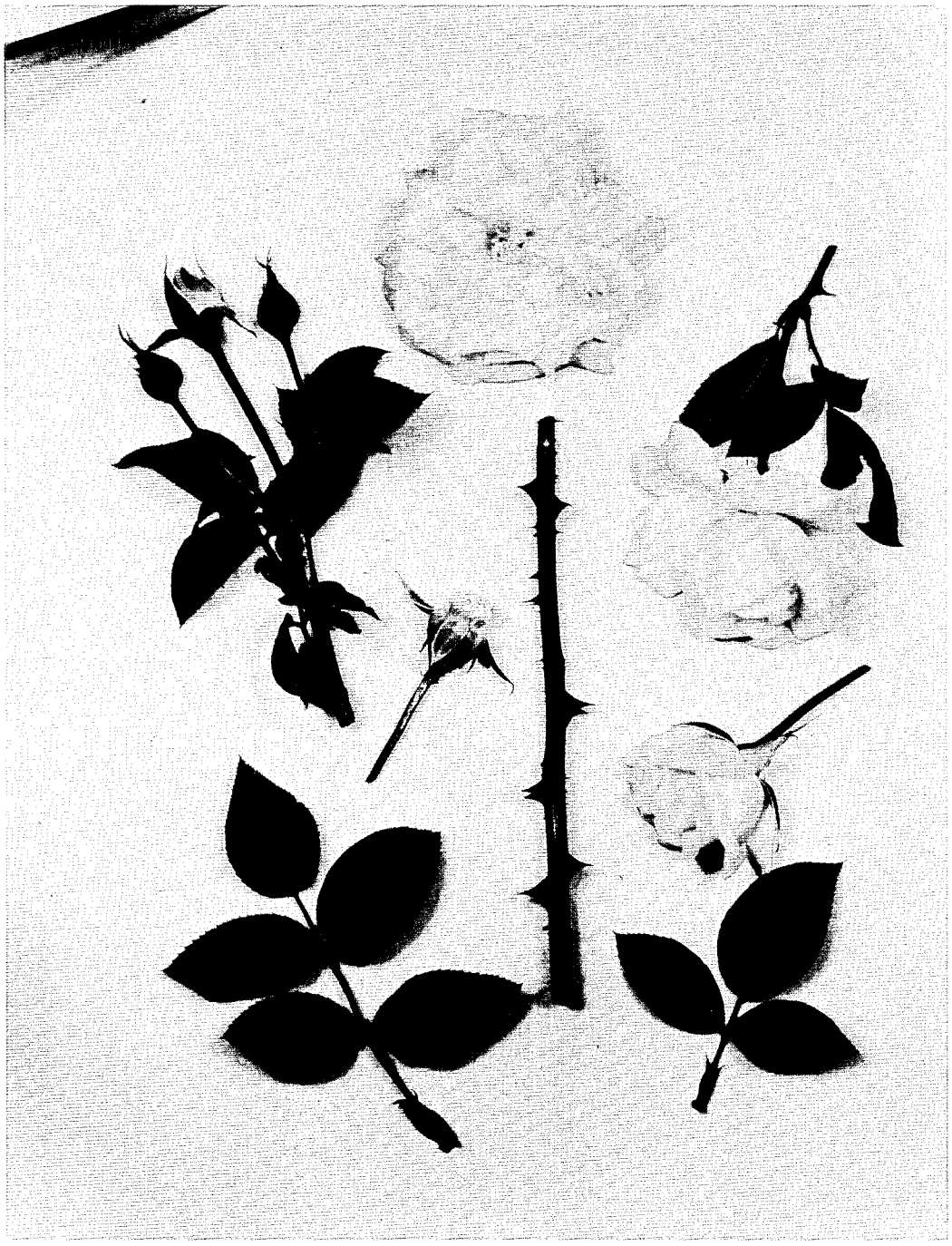
Inventor
Herbert C Brownell United States Patent Office Plant Pat. 2,960
Patented Jan. 20, 1970

2,960
ROSE PLANT

Herbert C. Brownell, Little Compton, R.I. 02837

Filed Mar. 22, 1968, Ser. No. 715,451
Int. Cl. A01h 5/00
U.S. Cl. Plt.—16 1 Claim My invention relates to roses and especially to a new, original and distinct variety of the class known commercially as "hybrid tea" and is a variant in that class, being a *Rosa wichuraiana* hybrid tea hybrid, produced by me and under my direction in the breeding grounds of my research gardens in Little Compton, R.I., by selection of variety variations and by cross pollination, which can be and has been asexually reproduced.

My new rose plant is new as to the following characteristics and especially as to their joint association with the characteristics inherited from *Rosa wichuraiana,* of hardiness, or immunity from serious injury on account of cold temperatures prevailing in certain parts of the northern United States.

The deep orange color (ordinary dictionary definition) of its petals in combination with the unique brilliance thereof and their tendency to hold these colors under exposure, fading only very slightly under direct rays of the sun.

The novelty and variation within certain definite limits of the form of the bloom, the recurl of the petals as the flower opens, its character of holding its form for a long time and the petalage of the flowers;

Its unusual abundance of flowers, at bloom time and after early bloom time until frost;

Its character of ascending in height by recurrent branching and progressively longer stems from the base;

The character of producing many seven leafleted leaves, which character seldom has obtained on hybrid teas not having *Rosa wichuraiana* ancestry;

And especially its characteristic of freedom from premature defoliation by blackspot, under certain definite conditions of exposure, without any cultural control.

The accompanying drawings shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Wilson's Horticultural Colour Chart, except where general color terms of ordinary dictionary significance are obvious:

Type: Hardy; bush; outdoor; seedling; for cut flower and garden decoration.
Class: Hybrid tea.
Breeding: Seedling.
*Seed parent.*—Tip Toes—Plant Patent Number 849.
*Pollen parent.*—Queen Elizabeth — Plant Patent Number 1,259.
Propagation: Holds its distinguishing characteristics through succeeding propagations by budding.

FLOWER

Locality where grown and observed: Little Compton, R.I., U.S.A.
Flowers borne: Singly and in clusters on stems of medium length and normal strength.
Quantity of bloom: Abundant, outdoors.
Continuity: Continuous during growing season until frost.
Fragrance: From slight to moderate.
Bud:
*Peduncle.*—Average length; medium caliper; moderate number of very fine red hairs. Color—Lettuce Green, Plate 861/2.

*Before calyx breaks.*—Size—medium. *Form*—short; oval; with foliaceous appendages on the surface of the bud; with foliaceous parts extending unevenly beyond the tip of the bud equal to ⅓ or more of its length. Color: outside—Lettuce Green 861/1; inside—Pod Green 061/2.
*As first petal opens.*—Color: outside of petal—Burnt Orange 014/1; inside of petal—Fire Red 15/1.
*Opening.*—Opens well outdoors with recurl of petals.
Bloom:
*Size (when fully open).*—Medium large; from 4 to 4½ inches.
*Petalage.*—Double; from 40 to 45 petals; arranged regularly.
*Form.*—Globular, becoming cupped. Petals recurl as bloom opens.
Petals:
*Texture.*—Thick with both inside and outside satiny.
*Shape.*—Obovate; no notches.

This description of a newly opened flower was made from a rose grown in the fields in the month of August at Little Compton, R.I.

*Color.*—Outside of petal: Shrimp Red 616/1. Inside of petal: Vermilion 18/2. At base of petal both inside and outside is a splash of Canary Yellow 2/2. These colors hold true on both outer and inner petals. General color effect of newly open bloom Poppy Red between Plate 16/1 and 16/2.
*Flower longevity.*—Cut roses picked in the fields as buds and brought into the house last five to seven days at normal room temperatures.

REPRODUCTIVE ORGANS

Stamens: Average number; fairly even.
Filaments: Average number; all with anthers, medium length. Color—Orange 12/1.
Anthers: All open at once; medium sized. Color—Sulphur Yellow 1/2.
Pollen: Abundant.
Pistils: Many; slightly irregular.
Styles: Uneven; short to medium length; small caliper. Color—Mimosa Yellow 602/2.
Stigma: Color—Canary Yellow 2/3.
Ovaries: Encased in calyx.
Hips: Rarely self pollinates but will with foreign pollen.
Sepals: Permanent; long pointed appendiculate.

PLANT

Foliage:
*Leaves.*—Compound of usually 3 to 7 leaflets; normal quantity; medium size.
*Leaflets.*—Shape—oblong lanceolate; pointed apex. Base—round. Margin—simply serrate.
*Color.*—Mature: upper surface — Parsley Green 00962; under surface—Parsley Green 00962/3. Young: upper surface—Parsley Green 00962; under surface—Sage Green 000861/1.
*Rachis (the supporting stem of the compound leaf).*—Slightly grooved. Under side—smooth with an occasional single prickle. Average size.
*Stipules.*—Medium in length and width with points of medium length, the upper of which normally form an angle of about 45 degrees.
*Disease resistance.*—Better-than-average resistance to blackspot and mildew as compated with other varieties grown under comparable conditions at Little Compton, R.I.
Growth:
*Habit.*—Bushy; upright-spreading; much-branched.
*Growth.*—Vigorous.
*Canes.*—Medium caliper.

*Main stems.*—Color—Sage Green 000861. Abundant prickles; not hooked; medium length; color—Garnet Brown 00918/3. No hairs.

*New shoots.*—Color—Fern Green 0862/1. Prickles—abundant; same color as main stems. Hairs—none.

I claim:

1. A new and distinct variety of rose plant of the hybrid tea type, substantially as herein shown and described, characterized particularly as to novelty by its vigorous habit of growth, abundant foliage, its resistance to mildew and blackspot, and its ability to withstand moderate sub-zero temperatures in combination with its hybrid tea character and its *Rosa wichuraiana* ancestry.

No reference cited.

ROBERT E. BAGWILL, Primary Examiner